(12) United States Patent
Freel et al.

(10) Patent No.: US 6,485,841 B1
(45) Date of Patent: Nov. 26, 2002

(54) BIO-OIL PRESERVATIVES

(75) Inventors: Barry Freel, Greely (CA); Robert G. Graham, Nepean (CA)

(73) Assignee: Ensyn Technologies, Inc., Greely (CA)

(*) Notice: Subject to any disclaimer, the term of this patent is extended or adjusted under 35 U.S.C. 154(b) by 0 days.

(21) Appl. No.: 09/182,964

(22) Filed: Oct. 30, 1998

(51) Int. Cl.$^7$ ................................................. B32B 9/02
(52) U.S. Cl. ........................ 428/498; 106/18; 106/18.32; 252/399; 252/404; 428/541; 530/500; 530/504
(58) Field of Search ............................... 428/323, 498, 428/541; 530/500, 504; 106/18, 18.32; 252/399, 404

(56) References Cited

U.S. PATENT DOCUMENTS

| | | | |
|---|---|---|---|
| 4,209,647 A | | 6/1980 | Galliron et al. |
| 4,234,665 A | * | 11/1980 | Johnston ................ 428/541 |
| 4,288,249 A | * | 9/1981 | Amundsen et al. ...... 106/18.35 |
| 4,354,316 A | * | 10/1982 | Schroder ................ 34/13.8 |
| 4,379,810 A | * | 4/1983 | Amundsen et al. ........ 428/541 |
| 4,382,105 A | * | 5/1983 | Amundsen et al. ........ 427/370 |
| 4,461,721 A | | 7/1984 | Goettsche et al. |
| 4,649,065 A | * | 3/1987 | Hein et al. ................ 427/370 |
| 4,778,833 A | | 10/1988 | Van der Drift et al. |
| RE33,121 E | | 11/1989 | Kirchner |
| 4,942,269 A | | 7/1990 | Chum et al. |
| 4,988,576 A | * | 1/1991 | Lin et al. ................ 428/537 |
| 5,098,472 A | * | 3/1992 | Watkins et al. .......... 106/15.05 |
| 5,129,946 A | | 7/1992 | Evans |
| 5,246,739 A | * | 9/1993 | Lin ..................... 427/393 |
| 5,378,323 A | | 1/1995 | Fransham et al. |
| 5,853,766 A | * | 12/1998 | Goettsche et al. .......... 424/632 |

FOREIGN PATENT DOCUMENTS

| | | |
|---|---|---|
| DE | 44 39 341 A1 | 5/1996 |
| DE | 4439 341 A1 | 9/1996 |
| EP | 0529 203 A1 | 5/1992 |
| EP | 0 529 203 A1 | 3/1993 |
| WO | WO 91/11499 | 8/1991 |

OTHER PUBLICATIONS

PCT International Search Report for corresponding International Application PCT/CA 99/00984, dated Feb. 18, 2000.
Derwent Publications, WPI Abstract for XP–002129927, Yang, B., Patent No. CN 1,106,449A (Aug. 1995).
Derwent Abstract of DE 443 934 1 (1 page) No Date.
Dr. Darrell D. Nicholas et al., IRG/WP 96–20083, Use of Compression Strength Loss for Measuring Decay In the Soil Block Test, Mar. 1996.

* cited by examiner

*Primary Examiner*—H. Thi Le
(74) *Attorney, Agent, or Firm*—Brinks Hofer Gilson & Lione

(57) ABSTRACT

The present invention is directed to bio-oil compositions, derived from fast pyrolysis of wood feedstocks, that exhibit properties of a preservative. The bio-oil may be used alone, in formulations with either a waterbased, or an oilbased, or a combination of a water based and an oil based preservatives. This invention also includes a method of preparing a wood preservative composition comprising, processing treated wood containing a preservative using a fast pyrolysis reactor, and obtaining the bio-oil fraction. The application of wood products with the bio-oil of the present invention is also disclosed.

32 Claims, 11 Drawing Sheets

BIO-OIL PRESERVATIVES

The present invention relates to the preparation and use of bio-oil as a preservative. More specifically, this invention is directed to the use of bio-oil as a wood preservative, either alone or in combination with other preservatives. Furthermore, this invention relates to methods for recycling wood preservatives treated wood products.

BACKGROUND OF THE INVENTION

Wood preservatives are required to extend the service life of wood beyond what would normally be available if the wood was left untreated and exposed to the natural process of biodegradation. Presently, wood preservative fall into two basic classes: oil based and water based. The major oil based preservatives are creosote and pentachlorophenol (PCP). Copper, chromium, arsenate (CCA) is the most commonly used water based preservative.

There is an interest within the wood preservative industry to find an environmentally friendly means of treating wood products. Furthermore, there is a general lack of suitable disposal alternatives for treated wood taken out of service. Land filling of wood waste is the current disposal solution. However, wood is bulky, low density, and does not compact well in the landfill and there is a growing desire to find a solution to the treated wood waste problem and therefore increase the life span of the landfill.

The processing of carbonaceous feedstocks to produce heat, chemicals or fuels can be accomplished by a number of thermochemical processes, one such process being pyrolysis. Pyrolysis is character by the thermal decomposition of materials in the relative absence of oxygen (i.e., significantly less oxygen than required for complete combustion). Typically, pyrolysis refers to slow conventional pyrolysis whose equilibrium products included roughly equal proportions of non-reactive solids (char and ash), secondly liquids, and non-condensible gases. However, over the past two decades fundamental pyrolysis research has unexpectedly indicated that high yields of primary, non-equilibrium liquids and gases (including valuable chemicals, chemical intermediates, petrochemicals and fuels) could be obtained from carbonaceous feedstocks through fast (rapid or flash) pyrolysis at the expense of undesirable, slow pyrolysis products. In other words, the low-value product distribution of traditional slow pyrolysis can be avoided by the approach embodied by fast pyrolysis processes.

Fast pyrolysis is a generic term that encompasses various methods of rapidly imparting a relatively high temperature to feedstocks for a very short time, then rapidly reducing the temperature of the primary products before chemical equilibrium can occur. By this approach the complex structures of carbonaceous feedstocks are broken into reactive chemical fragments which are initially formed by depolymerization and volatilization reactions, but do not persist for any significant length of time. Thus, non-equilibrium products are preserved, and valuable, reactive chemicals, chemical intermediates, light primary organic liquids etc may be obtained.

Fast pyrolysis is an intense, short duration process that can be carried out in a variety of reactor systems. The common aspect of these reactors is the ability to achieve extremely rapid feedstock heating with limitation of the reaction to relatively short times by rapid cooling which stops the chemical reactions before the valuable intermediates can degrade to non-reactive, low-value final products. A fast pyrolysis process reactor system typically provides for a very rapid feedstock heating rate, typically within the range of 1,000. degree. to 1,000,000. degree. C. per second. The elevation in reaction temperature is controlled and lies within the range of 350. degree. to 800. degree. C. The reaction/residence time is also controlled and short and lies within the range of 0.03 seconds to 2 seconds. Fast pyrolysis is also characterized by a rapid product quench where the products are quickly cooled below 350. degree. C. within 0.5 seconds. An example of such a process is found in U.S. Pat. No. 5,792,340 which discloses the conversion of wood and other biomass residues to a non-viscous liquid product, termed "bio-oil".

The processing of preservative treated wood via pyrolysis is possibly an option for recycling creosote or pentachlorophenol based wood preservatives. For example, U.S. Pat. No. 5,378,323 discloses the thermolysis of oil or tar based wood preservatives from sawdust and shavings obtained from the outer layer of treated telephone poles. The use of a fast pyrolysis reactor involving an inorganic particulate heat carrier for the recycling of these preservatives is not disclosed, nor are any of the properties of the product produced as a result of this process disclosed.

The present invention is directed to the use of bio-oil, obtained from the fast pyrolysis of wood biomass, as a preservative. Furthermore, bio-oil may also be mixed with traditional oil-based preservatives and be used either as a preservative carrier, or as an active ingredient within these novel compositions.

This invention also pertains to the recycling of wood treated with preservatives using fast pyrolysis to produce a bio-oil with properties suitable for use as a wood preservative. Results present herein demonstrate that bio-oil obtained from the fast pyrolysis of wood treated with creosote is as, or is more, effective than commercial grades of creosote.

Furthermore it has been noted that bio-oil adds to the strength of wood treated with bio-oil and acts not only as a preservative, but also to wood strengthening agent. Bio-oil also forms a protective skin on the exterior of the treated wood and acts as a physical barrier to decay.

SUMMARY OF THE INVENTION

The present invention relates to the preparation and use of bio-oil as a preservative. More specifically, this invention is directed to the use of bio-oil as a wood preservative, either alone or in combination with other preservatives. Furthermore, this invention is related to methods for recycling wood preservatives from treated wood products.

According to the present invention there is provided a bio-oil composition comprising derivatized lignin, alcohol, natural organic acids, carbonyls that is liquid at room temperature, wherein said bio-oil exhibits properties of a preservative. This bio-oil composition may further be characterized in comprising 2-methoxy-4-methylphenol and 3,4-dimethoxybenzoic acid.

This invention is also directed to a wood preservative composition comprising the bii-oil composition as defined above and a water based, or an oil based, or a combination of a water based and an oil based preservative. Preferably the bio-oil composition comprises an oil based preservative. Furthermore, it is preferable that the oil-based wood preservative is selected from the group consisting of creosote or pentachlorophenol.

This invention also embraces a wood product treated with any of the bio-oil compositions as defined above.

This invention also relates to a method of preparing a wood preservative composition, the wood preservative composition comprising the bio-oil composition as defined above and an oil based preservative, the method comprising processing wood treated with the oil based preservative using a fast pyrolysis reactor, and obtaining the resultant bio-oil fraction. Preferably, this method uses wood treated with creosote or pentachlorophenol as the feedstock for fast pyrolysis. This invention is also directed to a wood product treated with the wood preservative composition as defined above.

This invention also embraces a method of preparing a wood preservative composition comprising, heating bio-oil and adding a waterbased, or oilbased, or a combination of a water based and an oil based preservative to the bio-oil, followed by cooling the wood preservative composition to room temperature.

The present invention also provides a method of sealing a wood product comprising treating said wood product with any of the bio-oil compositions defined above.

This invention also relates to a method for increasing the strength of a wood product comprising treating the wood product with any of the above bio-oil compositions.

This invention also embraces a method of recycling preservative-treated wood products comprising:
  i) processing the preservative-treated wood products within a fast pyrolysis reactor;
  ii) obtaining a bio-oil fraction; and
  iii) treating a wood product with said bio-oil fraction.
Furthermore, steps i) to iii) this method may be repeated.

The present invention is directed to the use of bio-oil as a preservative agent. Furthermore, this invention is directed to novel bio-oil compositions that are effective in wood preservative applications and exhibit several desirable properties including increased preservative qualities, increased wood strength, the formation of a protective coating of the wood product, and pleasant wood colouration. Furthermore, this invention provides for a method of recycling treated wood products and demonstrates the suitability of the re-use of the resultant bio-oil product within preservative applications.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
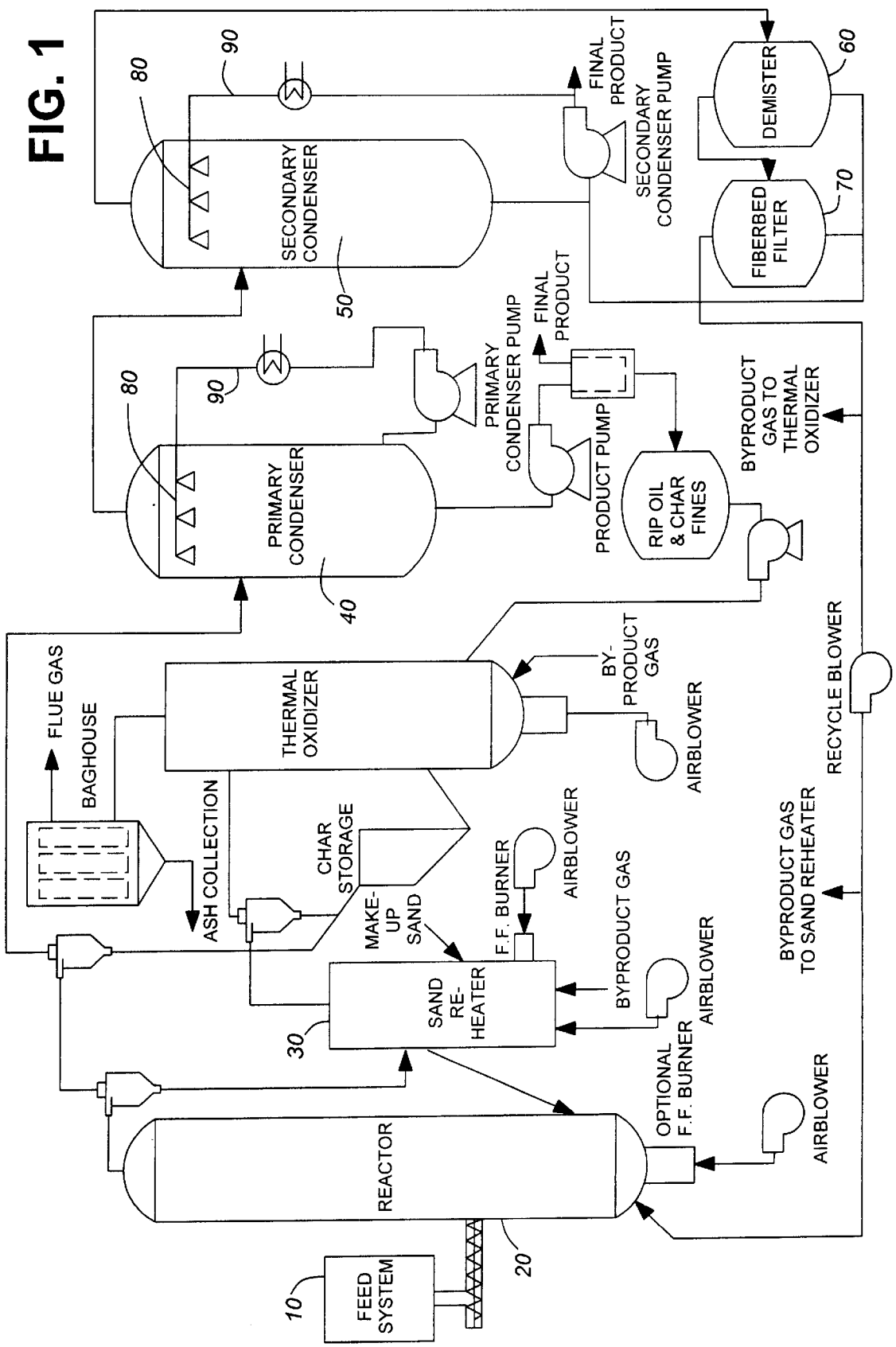
FIG. 1 shows a schematic of a fast pyrolysis system.

The present invention relates to the use of bio-oil as a preservative. More specifically, this invention is directed to the use of bio-oil as a wood preservative, either alone or in combination with other preservatives. Furthermore, this invention relates to methods for recycling wood preservatives from treated wood products.

By "bio-oil" it is meant the liquid fraction obtained following the fast pyrolysis of wood. The bio-oil is obtained from the product vapour which is produced along with char following pyrolysis. Upon removal of the char the product vapour is condensed and collected within one or more condensers which are typically linked in series. Bio-oil refers to the combination of the condensed products obtained from all of the condensers. Both hardwoods and softwoods, and residues derived from either of these woods can be used as feedstock for the purposes of the invention as described herein. Furthermore, as is described in more detail below, wood-products already treated with preservatives, and associated treated wood product residues may also be used as feedstock for the preparation of bio-oil.

When produced from wood, associated residues, or treated wood, bio-oil consists of depolymerized wood components which are made up primarily of carbon, hydrogen and oxygen. Sulphur levels are extremely low, typically negligible. The major organic constituents in bio-oil are a liquid lignin derivative (depolymerized "liquid" lignin), alcohols, natural organic acids, and carbonyls. Water is also a major component and is fully miscible in the bio-oil. Bio-oil is a non-viscous, oxygenated organic liquid which is pourable and pumpable at room temperature.

Bio-oil is characterized with the following ingredients:
  a water content from about 15 to about 30%, typically from about 22–24%,
  pyrolytic lignin from about 20 to about 30%,
  from about 10 to about 20% carboxylic acids (acetic, formic, propionic and glycolic as the major carboxylic acids, with butyric, pentanoic and hexanoic present in small amounts),
  aldehydes of from about 14 to about 25% (primarily glycoaldehyde, glyoxal, hydroxypropanol, methyl glyoxal, and to a lesser amount formaldehyde, acetaldehyde 2-furaldehyde and syringaldehyde),
  from about 5 to about 15% sugars (levoglucosan, fructose, cellobiosan and glucose, along with others at lower concentrations including various oligosaccharides, andydroglucofuranose),
  ketones from about 4 to about 10% (primarily hydroxypropane, cyclopentanone, cyclopentene, furanone, hydroxymethylpyrone, and others at lower concentrations including butyrolactone, acetyloxyprapanone),
  alcohols from about 2 to about 10% (acetol, methanol, ethylene glycol),
  from about from about 2 to about 8% solids content.
  a viscosity of from about 30 to about 80 cSt (@50° C.),
  a density of >1,1 tm$^3$ (@15° C.), a specific gravity of from about 1.15 to about 1.25, typically about 1.2.

The bio-oil of the present invention is different from the products obtained from wood conversion processes such as slow pyrolysis that result in 20–30% yields, and a thick polymerized "tar" product.

The bio-oil of the present invention is prepared using a fast pyrolysis reactor, and such pyrolysis systems are known within the art, for example U.S. Pat. No. 5,792,340, or WO 91/11499. Fast pyrolysis of wood, associated residues, or treated wood results in the preparation of product vapours and char. After removal of the char components from the product steam, the product vapours are condensed to obtain a bio-oil product from pyrolysis. With reference to FIG. 1, briefly, the system includes a feed system (10), a reactor (20), a particulate inorganic heat carrier reheating system (30), and for the purposes of the invention described herein, primary (40) and secondary (50) condensers, through which the product vapours produced during pyrolysis are cooled and collected using a suitable condenser means (80). However, it is to be understood that analogous fast pyrolysis systems, comprising differences in the reactor processes, or that utilize an alternative heat carrier, or different numbers or size of condensers, or different condensing means may be used for the preparation of the bio-oil of this invention.

Preferably, the bio-oil comprises chemical properties that are suitable for use as a wood preservative as described herein. Furthermore, it is preferred that the reactor is capable of producing high yields of bio-oil, for example from about 60 to about 80% of the feedstock. Without wishing to limit the scope of the invention in any manner, an example for the suitable conditions for a the pyrolytic treatment of feedstock, and the production of bio-oil is described in U.S. Pat. No. 5,792,340 and utilizes an inorganic particulate heat carrier, such as sand. This process include a reactor temperature from about 520° to about 1200° C.; loading ratios of particulate heat carrier to feedstock from about 5:1 to about 200:1, and residence times from about 0.35 to about 0.7 sec. With this system the residence times can be carefully regulated in order to optimize the processing of the feedstock and bio-oil yields. However, it is to be understood that while this fast pyrolysis system is preferred, other pyrolysis systems that are capable of producing a bio-oil with characteristics that are suitable for use as a wood preservative, as described herein, may be also be used.

As will be described in more detail below, preliminary wood penetration tests conducted using bio-oil prepared using fast pyrolysis indicate that bio-oil is effective as a natural wood preservative. Chemical analysis of a typical bio-oil reveals several chemicals that inhibit the growth of fungi. These chemicals include, but are not limited to, lignin-derived phenolic compounds and their derivatives. In addition, bio-oil contains components that polymerize upon exposure to air forming a solid skin. Therefore, following treatment of wood, bio-oil forms a continuous coating that seals the wood surface, locking in the preservative to prevent leaching, and also inhibit water penetration. This property may be desired in using bio-oil alone, or when bio-oil is used along with another wood preservative that are known to become depleted when applied to wood surfaces, for example, but not limited to, pentachlorophenol (penta) preservatives. Therefore, formulations comprising bio-oil and another preservative may be desired in order to treat a wood product.

Wood products treated with bio-oil, or bio-oil formulated preservatives have a pleasing colour, which may be darkened if desired depending upon the application.

It has also been observed that the mechanical strength, and compressive resistance of wood treated with bio-oil increases with increased concentration of applied bio-oil. This feature may be desired within applications such as, but not limited to, hydro poles, rail-way ties, wooden building foundations, or landscaping materials and the like, where increased strength is desired and may lead to increased utility, for example the life span, of the wood product. However, it is to be understood that a variety of wood products may be treated with the bio-oil of this invention. If equivalent or better protection than that offered by virgin creosote or pentachorophenol is required than bio-oil compositions comprising creosote, or pentachlorophenol may be used. It is also considered within the scope of the present invention that other wood products, requiring less demanding preservative qualities (than those associated with creosote or pentachlorophenol), may be treated using bio-oil produced from virgin hardwoods. Such applications may include exterior lumber uses, decking, plywood, or other panelling materials, siding etc.

The addition of bio-oil to known preservatives may also be desired in order to compliment the properties of the desired preservative. In this manner, bio-oil may also be used as a carrier for a preservatives of either oilborne or waterborne preservatives. It is preferred that the preservatives are miscible with bio-oil, and in this manner, bio-oil may function as a replacement of the fuel oil or aqueous solvents now used in the industry. However, it is also within the scope of the present invention that bio-oil may function as an active ingredient within these preservative formulations, and complement the preservatives activity. For example, addition of bio-oil to pentachlorophenol preservatives may be desired since bio-oil exhibits superior activity against white rot fungus, thereby complimenting the lack of this activity in pentachlorophenol preservatives. It is also within the scope of the present invention that preservative formulations comprising bio-oil and creosote may also be used, since formulations comprising these two components exhibit better preservative properties against both white and brown-rot fungi than either bio-oil or creosote alone. It is to be understood that other bio-oil/preservative combinations may also be effective as wood preservatives, providing that the bio-oil is either miscible within the desired preservative, forms an emulsion with the preservative, or that the bio-oil be otherwise present within the formulation so as to exhibit a desired property to the formulation. Such a desired property may include, but is not limited to, enhancing the preservative quality of the treated wood, increasing the strength of the treated wood, sealing the treated wood, or modifying the colouring of the treated wood.

This invention is also directed to the processing and recycling of creosote-treated wood using fast pyrolysis. The bio-oil produced from this feedstock is shown to comprise characteristic compounds present in both creosote and bio-oil (see FIGS. 3 to 6), and gives rise to a novel bio-oil formulation that is very effective as a wood preservative. Furthermore, these novel formulations comprise additional properties as discussed above including increased strength, sealing etc, that may be beneficial for the treatment of a wood product. The feedstock comprising pre-treated wood may comprise the entire treated wood product that is chipped in order to be in a form that can be feed into the reactor. However, processed wood products, for example comprising the outer layer of hydro poles, as disclosed in U.S. Pat. No. 5,378,323, may also be used as feedstock as described herein.

Fast pyrolysis runs have produced bio-oil/creosote liquid yields of about 75% using treated wood feedstocks. From gas chromatographic analyses, it is apparent that the creosote compounds pass through the pyrolysis process largely unreacted, and soil-block assays that examine the preservative efficacy indicates that not only is the preservative activity of creosote undiminished following this treatment, but that the presence of bio-oil within creosote enhances the efficacy of creosote against both white and brown-rot fungi.

Figure 5:
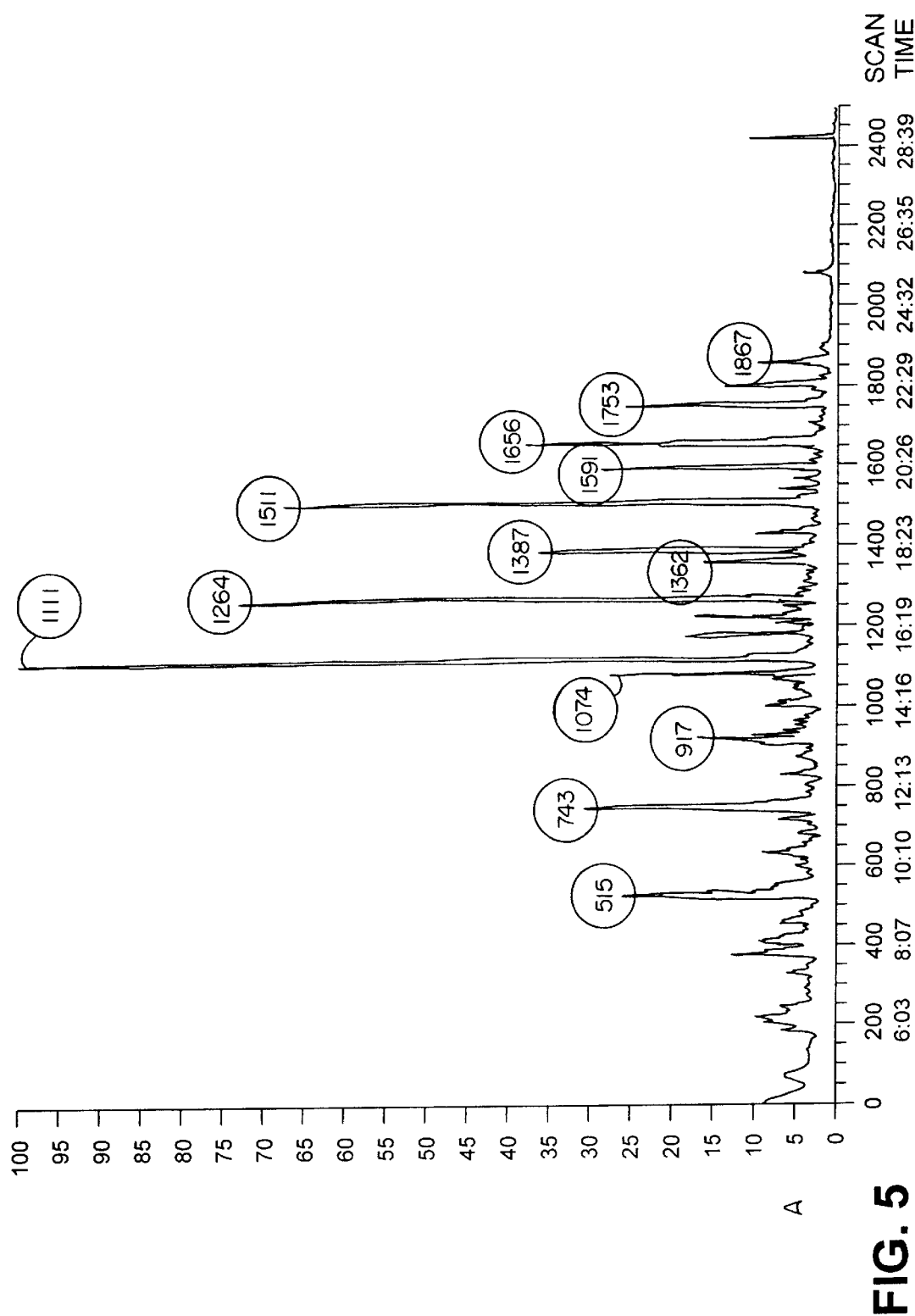
FIG. 5 shows a GC elution profile of bio-oil obtained from hardwood feedstock.
Figure 6:
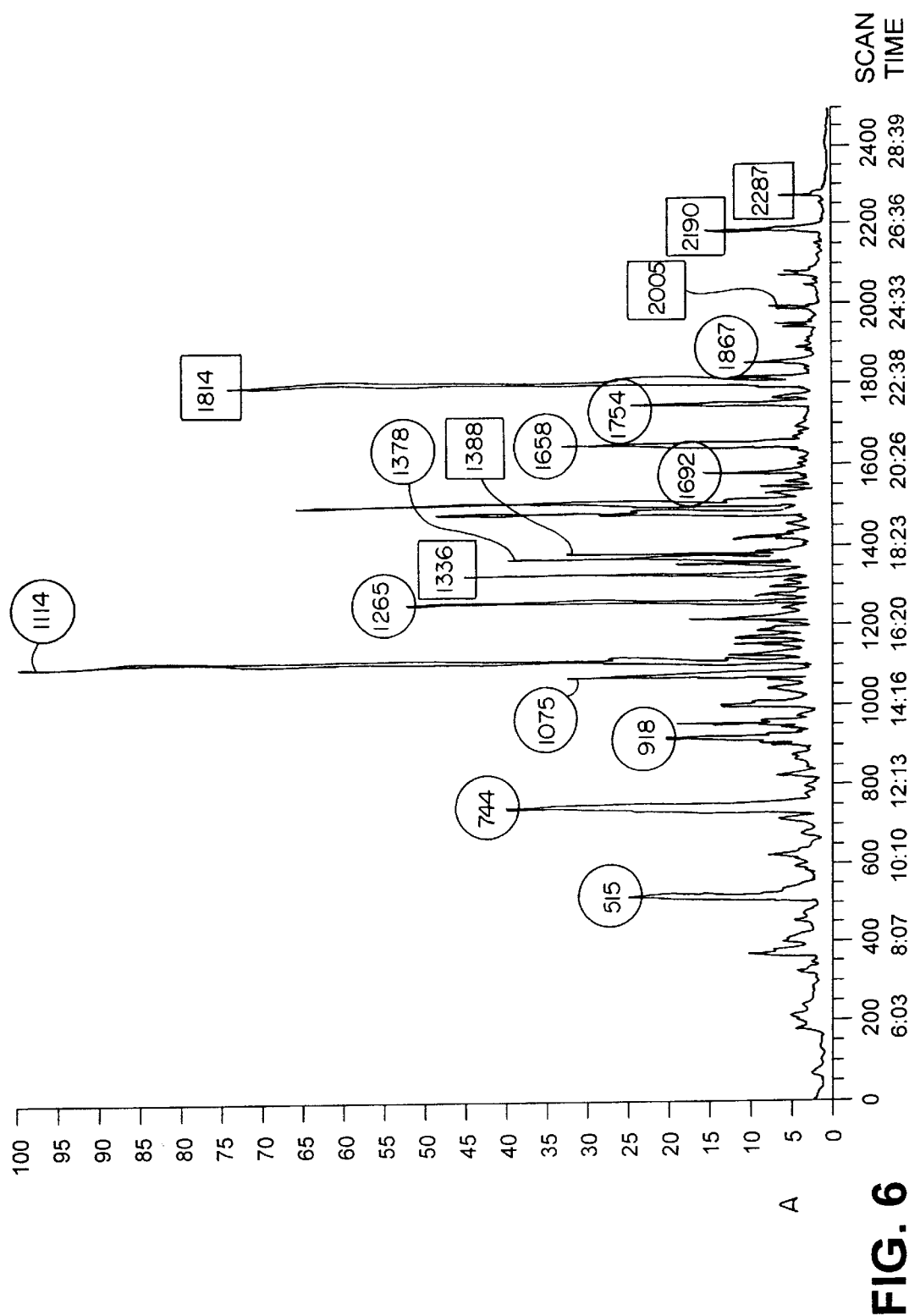
FIG. 6 shows a GC elution profile of bio-oil obtained from creosote treated (railway-tie) feedstock processed using fast pyrolysis.

The bio-oil of the present invention may be characterized by its general elution profile following GC analysis, such as that in FIG. 5, or in Table 1, for bio-oil prepared from wood, or FIG. 6, or Table 3 for bio-oil prepared from creosote treated wood. However, these figures and tables are to be considered as example of several desired bio-oil preparations, and it is to be understood that these elution profiles and chemical compositions are not to be considered limiting in any manner. As is evident from the analysis of the different bio-oil compositions disclosed herein, other bio-oil components may be present in bio-oil depending to the feedstock used for fast pyrolysis. Therefore, this invention includes a bio-oil produced using fast pyrolysis, providing that the bio-oil exhibits the characteristics associated with wood preservatives.

TABLE 1

Components found in Bio-oil Derived from Wood

| MS Spectral Scan Number* | |
|---|---|
| 517 | 2-methoxyphenol |
| 746 | 2-methoxy-4-methylphenol |
| 919 | 4-ethyl-2-methoxyphenol or 1,4-dimethoxy-2-methylphenol |
| 1077 | 2-methoxy-5-(or 4,6)(1-propenyl) phenol |
| 1119 | 2,6-(or 3,4-) dimethoxyphenol |
| 1173 | 2-methoxy-5-(or 4, or 6)(1-propenyl) phenol |
| 1267 | 4-hydroxy-3-methoxybenzoic acid or 2,5-dimethoxybenzyl alcohol |
| 1364 | (1,1-dimethylethyl)-1,2-benzenediol or 1-(4-hydroxy-3-methoxyphenyl)ethanone |
| 1389 | 3,4-dimethoxybenzoic acid |
| 1515 | 2,6-dimethoxy-4-(2-propenyl)-phenol |
| 1658 | 3,4' (or 3,3' or 4,4')-1,1'-biphenyl |

*see FIG. 5; these number indicate approximate elution positions following GC, variations in these numbers exist from run to run

TABLE 2

Components Found in the Inudustrial Creosote Sample

| MS Spectral Scan Number* | |
|---|---|
| 742(☐745) | naphthatene |
| 963 | 1-methylnaphthalene |
| 1341(☐1345) | 1,1'-biphenyl, or acenaphthalene, or 2-ethenyl-naphthalene |
| 1385 | dibenzofuran |
| 1498 | 9H-fluorene, or 1H-phenalene |
| 1820 | phenanthrene, or anthracene |
| 2287 | fluoranthene, or pyrene |

Figure 4:
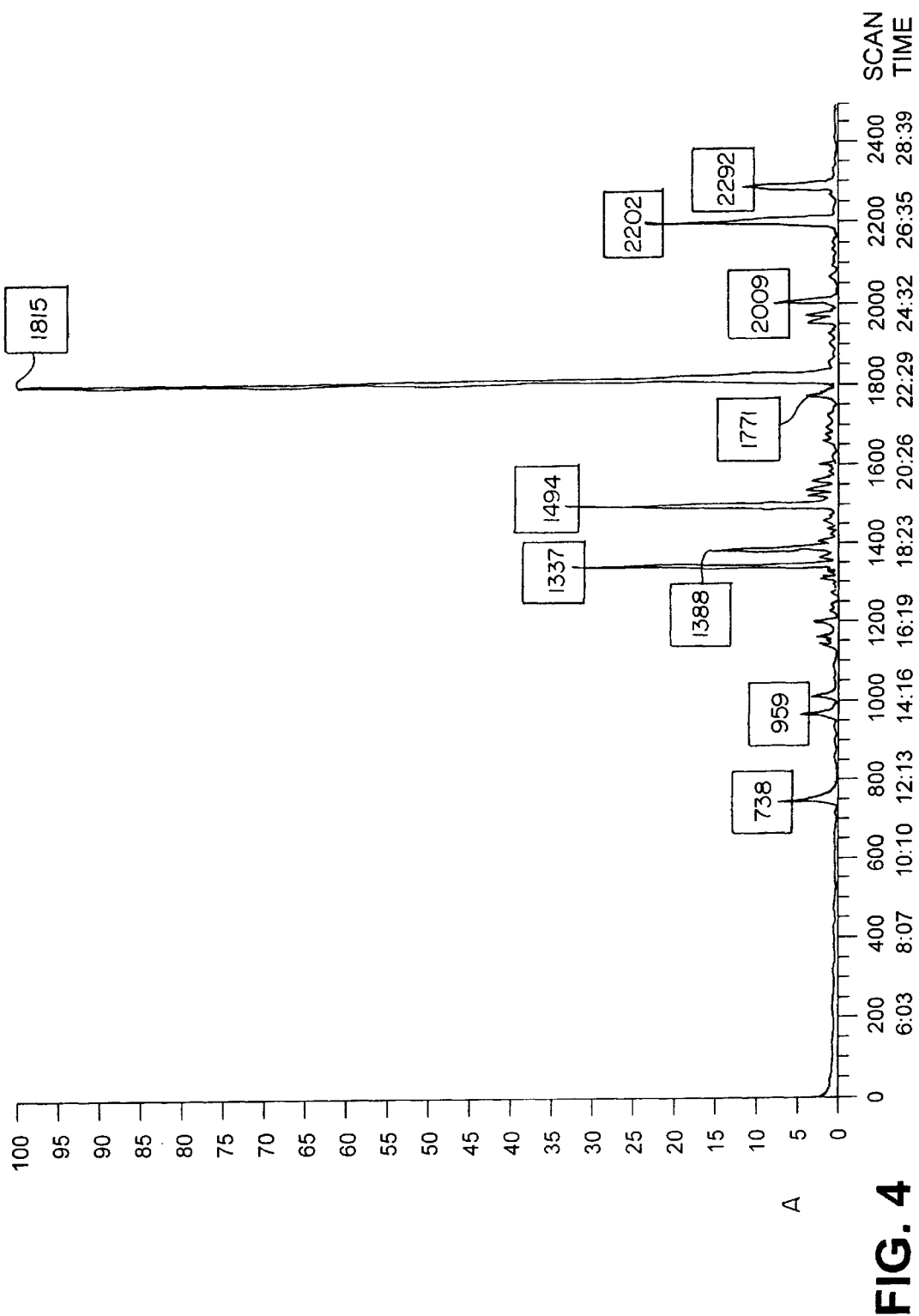
FIG. 4 shows a GC elution profile of creosote extracted from wood treated with creosote (railway-ties).

*see FIG. 4; these number indicate approximate elution positions following GC, variations in these numbers exist from run to run

TABLE 3

Components found in the Separated Creosote from Bio-Oil Sample

| MS Spectral Scan Number* | |
|---|---|
| 517 | 2-methoxyphenol |
| 746 | 2-methoxy-4-methylphenol |
| 919 | 4-ethyl-2-methoxyphenol or 1,4-dimethoxy-2-methylphenol |
| 957 | 1-(or 2-)methylnaphthalene |
| 1001 | 1-(or 2-)methylnaphthalene |
| 1077 | 2-methoxy-5-(or 4,6)(1-propenyl) phenol |
| 1119 | 2,6-(or 3,4-) dimethoxyphenol |
| 1129 | 1,1'-biphenyl, or acenaphthalene, or 2-ethenyl-naphthalene |
| 1173 | 2-methoxy-5-(or 4, or 6) (1-propenyl) phenol |
| 1223 | 3-hydroxy-4-methoxy (or 4-hydroxy-3-methoxy)-phenol |
| 1267 | 4-hydroxy-3-methoxybenzoic acid or 2,5-dimethoxybenzyl alcohol |
| 1336 | 1,1'-biphenyl, or acenaphthalene, or 2-ethenyl-naphthalene |
| 1364 | (1,1-dimethylethyl)-1,2-benzenediol or 1-(4-hydroxy-3-methoxyphenyl)ethanone |
| 1379 | dibenzofuran |
| 1389 | 3,4-dimethoxybenzoic acid |
| 1434 | 4-hydroxy-3-methoxy-benzeneacetic acid |
| 1493 | 9H-fluorene, or 1H-phenalene |
| 1515 | 2,6-dimethoxy-4-(2-propenyl)-phenol |
| 1658 | 3,4' (or 3,3' or 4,4')-1,1'-biphenyl |
| 1815 | phenanthrene, or anthracene |
| 1824 | phenanthrene, or anthracene |
| 2199 | fluoranthene, or pyrene |

Figure 11:
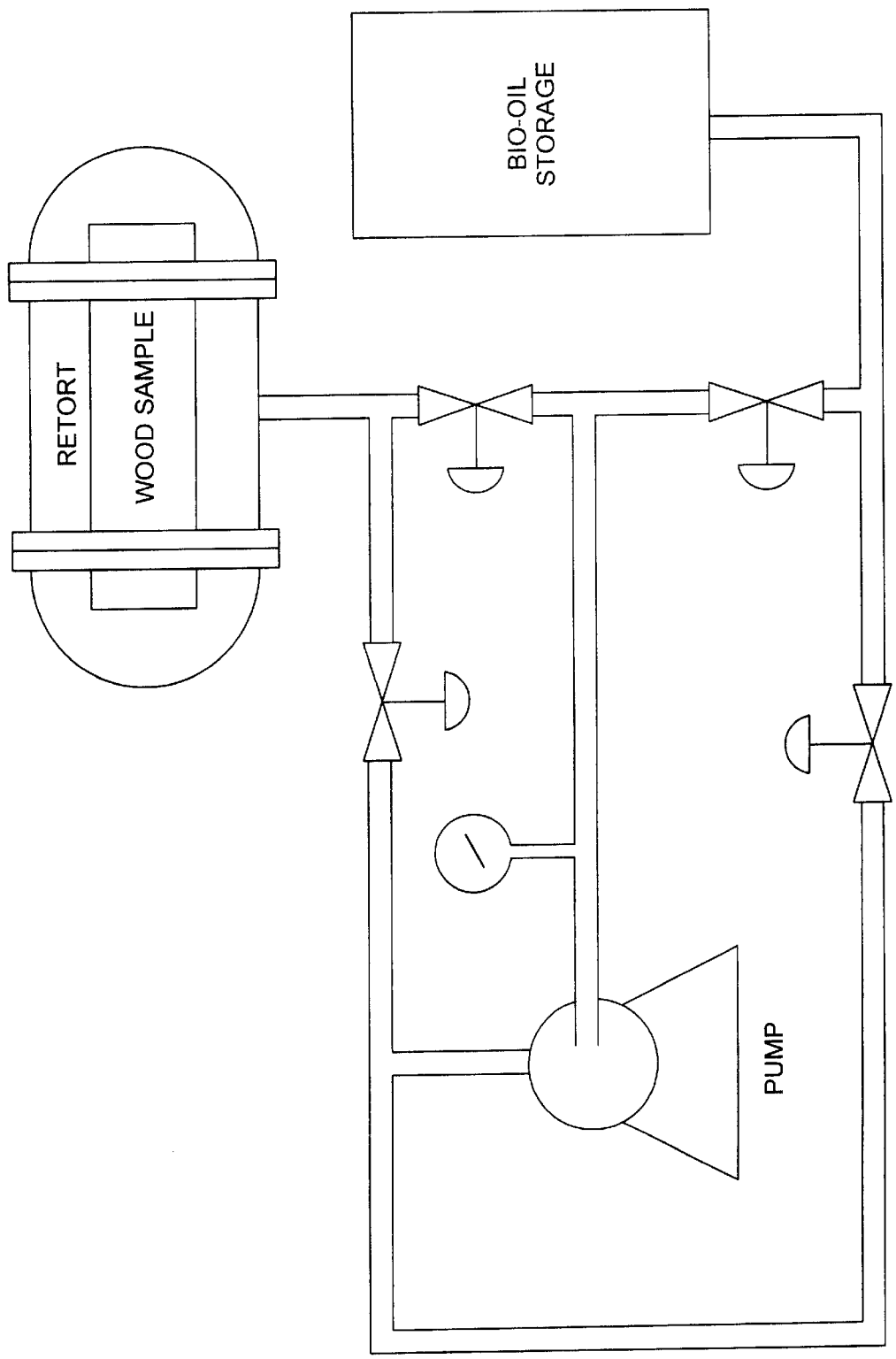
FIG. 11 shows a schematic for a wood treatment plant using the bio-oil of the present invention.

*see FIG. 6; these number indicate approximate elution positions following GC, variations in these numbers exist from run to run This invention is also directed to a plant for the pressure treatment of wood using bio-oil, or bio-oil-preservative formulations, such as that shown on FIG. 11. The plant is designed to handle typical wood products such as, but not limited to, a poles ties, lumber and the like. The retort may be heated to desired temperatures and pressures that are consistent with industry norms, or as required for the specific product desired. Treating solutions are cycled from storage tanks to the treatment baths or retorts. As preservative is used the tanks are topped up with fresh preservative. Preliminary data indicate that creosote containing bio-oils may be effectively recycled and replenished in this manner.

The present invention will be further illustrated in the following examples. However it is to be understood that these examples are for illustrative purposes only, and should not be used to limit the scope of the present invention in any manner.

EXAMPLES

Example 1

Recovery of Creosote from Treated Wood

Salvaged railway ties were obtained locally. A wood chipper was used to reduce the railway ties to a fraction capable of being feed into a fast pyrolysis reactor such as that described in U.S. Pat. No. 5,792,340. All wood exiting the grinder had a grain size of approximately 6 mm. Physical properties for the creosote treated wood are presented in Table 4.

TABLE 4

FEEDSTOCK ANALYSIS CREOSOTE WOOD

| Run Number | R152 | R155 | R156 | R157 | R158 |
|---|---|---|---|---|---|
| Moisture (wt %) | 3.9 | 8.8 | 9.0 | 9.1 | 9.1 |
| Ash Content (wt %) | 2.93 | 2.73 | 3.0 | 2.36 | 2.60 |

Conditions for pyrolysis treatment of the feedstock are as described in U.S. Pat. No. 5,792,340, and briefly include a reactor temperature from about 520° to about 1200° C. Loading ratios for particulate heat carrier to feedstock from about 5:1 to about 200:1, and residence times from about 0.35 to about 0.7 sec. These conditions are outlined in more detail below.

Sample R152 was oven dried. It was felt that some volatile components may be lost during oven drying and subsequent samples were air dried only, hence the higher moisture content. The ash content is higher than is normal for most wood (0.3 to 0.6 wt %). Salvaged railway ties have usually picked up dirt and sand during their service life. The pumping action of a train travelling over a tie can force particles into cracks or embed sand grains directly into the wood. The creosote on new ties may be tacky and conducive to picking up inorganic material during placement. As the creosote dries and hardens during use, the inorganic material becomes bonded to the tie and will increase the ultimate ash content. The creosote content of the feedstock was measured at 16% by weight. New ties have approximately the same content and confirms the notion that once creosote is impregnated into the wood it tends to remain there and does not biodegrade during the life span of the treated wood.

Creosote samples for gas chromatography were prepared from the feed stock ties by toluene extraction in a socket apparatus. The separation of creosote from bio-oil was accomplished using an acetone wash, a separation funnel and Rotovap apparatus.

Fast Pyrolysis of Creosote Treated Wood

Six fast pyrolysis runs were made on creosote treated wood. Five of the runs (R152, R155–R158) were used to determine system operating parameters, yields and liquids for analysis. The sixth run (R162) was made to obtain liquid bio-oil/creosote for soil block testing. Mass balances for the first five runs are presented in Table 5.

TABLE 5

MASS BALANCE RAILWAY TIES

|  |  | R152 | R155(1) | R156 | R157 | R158 |
|---|---|---|---|---|---|---|
| Reactor Temperature |  | 1047 | 995 | 865 | 970 | 1182 |
| Residence Time (ms) |  | 430 | 419 | 444 | 424 | 397 |
| INPUT |  |  |  |  |  |  |
| Feed (lbs) |  | 2.65 | 10.97 | 15.43 | 9.15 | 1.41 |
| OUTPUT |  |  |  |  |  |  |
| Gas (lbs) |  | 0.76 | 1.89 | 1.93 | 1.47 | 0.65 |
|  | Yield (%) | 28.7 | 17.5 | 12.5 | 16.1 | 46.1 |
| Char (lbs) |  | 0.24 | 0.94 | 1.55 | 0.80 | 0.13 |
|  | Yield (%) | 9.1 | 8.7 | 10.0 | 8.7 | 9.2 |
| Liquid(lbs) |  | 1.50 | 7.92 | 11.75 | 6.52 | 0.70 |
|  | Yield (%) | 56.6 | 73.4 | 76.2 | 74.5 | 49.6 |
| Closure(%) |  | 94.4 | 99.6 | 98.7 | 99.3 | 104.9 |

(1)Petroleum quench used as quench, all others used a bio-oil quench.

Figure 2:
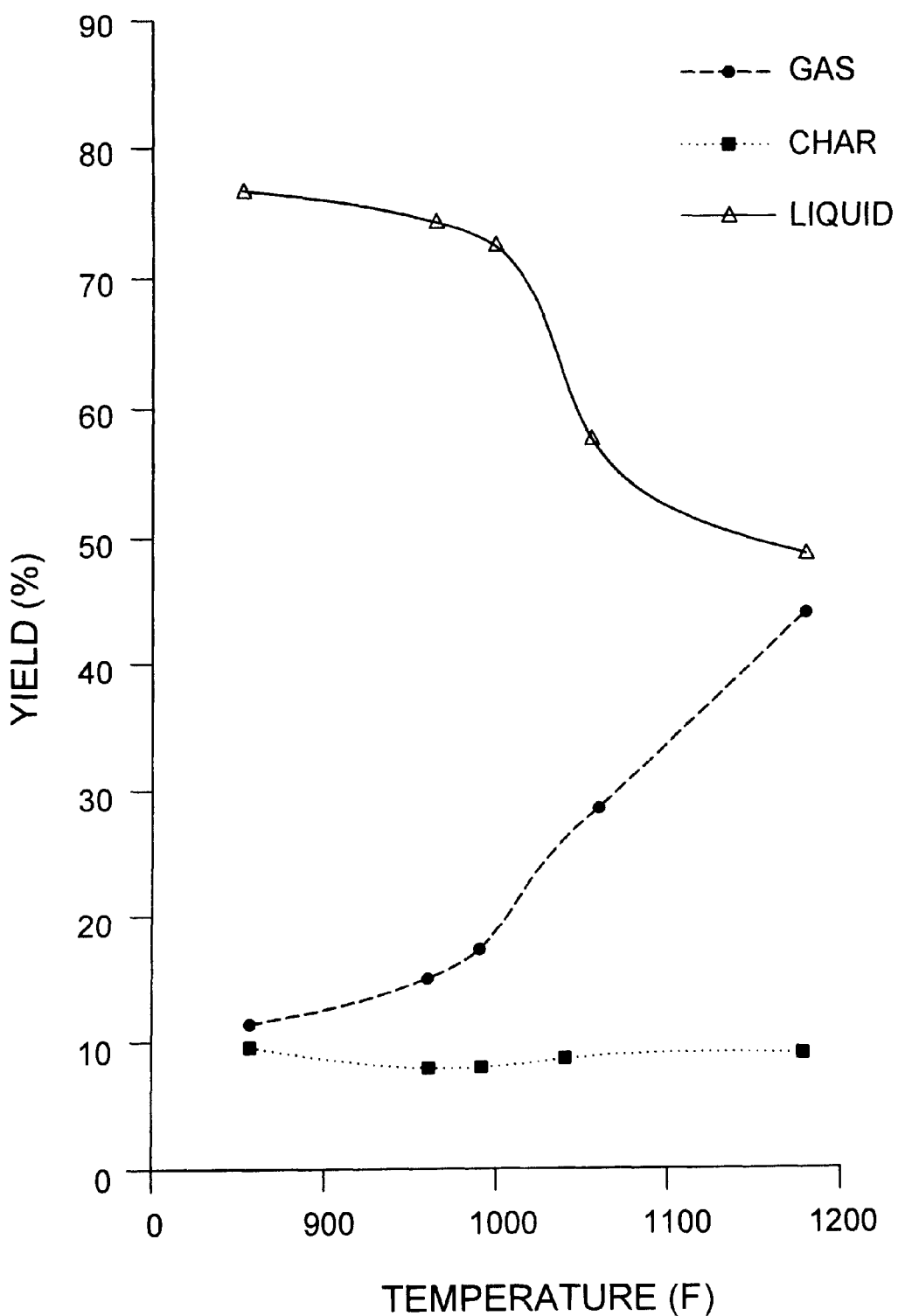
FIG. 2 shows a plot of the product yields of bio-oil compared with reactor temperature.

FIG. 2 shows a plot of the product yields versus the reactor temperature. There is a sharp break in the liquid yield curve between 1000° F. and 1047° F. Above 1000° F. liquid yields decrease rapidly and there is a corresponding increase in gas yield. A maximum liquid yield was not obtained over the reactor temperatures used in this set of runs. Normally the liquid yield for wood is a maximum between 915° F. and 959° F. Run R156 at a reactor temperature of 865° F. had a liquid yield of 76.2%. The maximum liquid yield is obtained between about 800° F. to about 900° F. Overall the char yield remained constant at between 8.7% and 10.0%. There does not appear to be a dependence of char yield on reactor temperature.

Based on the data presented in Table 5, a subsequent run (R162) at 1000° F. was carried out and the resulting liquid submitted for soil block testing (see Example 3).

Creosote Characterization

Samples of: commercial creosote; creosote extracted from railway ties; bio-oil from hardwood; and creosote extracted from big-oil obtained from railway ties, were characterized by Gas Chromatography in order to compare creosote from different sources with that of a standard bio-oil. Gas chromatographs for the four samples are shown in FIGS. 3 to 6.

Figure 3:
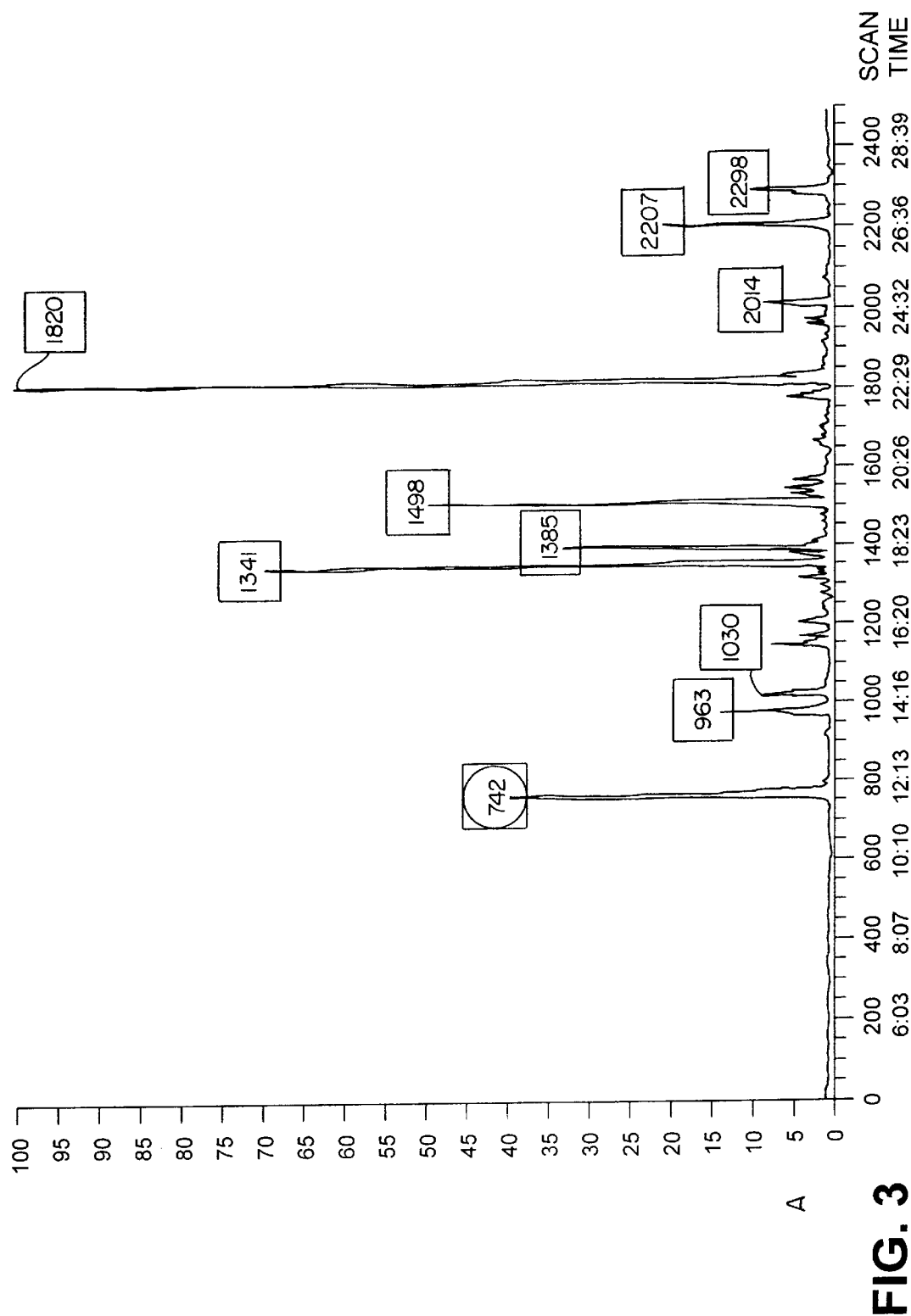
FIG. 3 shows a GC elution profile of virgin creosote.

A comparison of FIGS. 3 and 4 indicates that there is little difference between a new commercial creosote with that of the aged creosote extracted from railway ties. With the exception of the peak between 1815 and 1820 the peaks of the extracted sample are of lower intensity suggesting that sonic of these compounds may have degraded over time. In general terms creosote can be characterized by seven spectral peaks, 742, 963, 1341, 1385, 1498, 1820 and 2287.

The gas chromatograph spectra for the bio-oil control sample is shown in FIG. 5. The complexity of bio-oil is apparent in FIG. 5. Creosote has no compounds with spectra less than 742 whereas big-oil has a strong peak at 515 (2-methoxyphenol). Of the seven peaks that characterize creosote, bio-oil shares only 2: 742 (2-methoxy-4methylphenol) and 1387 (3,4-dimethoxybenzoic acid).

The creosote present in bio-oil is essentially a combination of the bio-oil spectra and the creosote spectra (FIG. 6). This is clear evidence that creosote is recovered during pyrolysis. Furthermore, the results suggest that the separation techniques employed, involving acetone extraction, filtering, and Rotovap did not remove all of the bio-oil from the creosote. Therefore the effect of bio-oil within the creosote was examined to determine if bio-oil can act as a wood preservative, and if bio-oil has a positive, neutral or negative effect on the efficacy of the recovered creosote as a wood preservative.

Example 2

Bio-Oil as a Preservative

Hardwood (containing no creosote) was processed in a fast pyrolysis system under conditions disclosed in U.S. Pat. No. 5,792,340. The recovered bio-oil (R151) was analysed using soil block testing (see below) to establish the toxic threshold value for the bio-oil against a brown-rot fungus, *Gloeophyllum trabeum* (*G. trabeum*) and a white-rot fungus, *Trametes versicolor* (*T. versicolor*). The results were compared against those obtained using creosote. Also several samples containing creosote alone, and bio-oil alone (as per example 1) were also tested. A range of concentrations of samples were used for this analysis, from 5 to 50% bio-oil, or from 5 to 25% creosote, with the remainder being methanol or methylene chloride. Methanol or methylene chloride (100%) were used as controls.

Soil block testing is a standard technique (AWPA E-10-91) for evaluating the efficacy of a wood preservative against white-rot and brown-rot fungi. This technique uses the mass loss of a soil block as a measure of decay. The test duration takes a minimum of 15 weeks. Nicholas and Jin (1996) developed a modified AWPA method using the compressive strenth of wood blocks and thereby reduced the incubation time from 15 weeks to 6 weeks.

Southern yellow pine and aspen sapwood was cut into blocks measuring 19 mm×19 mm×5 mm. The blocks were then numbered and separated into sequentially numbered pairs. One of the pairs served as the control specimen while the other was treated and subjected to decay testing. Aspen blocks were used in decay testing with white-rot while southern yellow pine was used for brown-rot testing.

One half of the blocks were placed in a vessel and placed under a vacuum of between 28 to 30 inches of Hg. Preservative was then introduced into the vessel and the vacuum removed. Preservative retention was established by weighing of samples before and after introduction of the preservative. The desired retention was governed by diluting the preservative with methanol or methylene chloride. Test results are reported as the loss (gain) in compressive strength as function of retention.

Aspen blocks were used in conjunction with white-rot fungus and southern yellow pine for decay testing with brown-rot fungus. After 6 weeks the samples were strength tested and the loss in strength was measured against the control block. The retention was varied for both preservatives to determine the fungus toxicity threshold.

Bio-oil exhibits fungicidal activity against both tested fungi. However, it is considerably more effective against white rot fungus, *T. versicolor* than brown-rot fungus, *C. trabeum* (see Table 6 and FIG. 7).

TABLE 6

FUNGICIDAL ACTIVITY OF WOOD PRESERVATIVES

| Treatment | Approximate Toxic Threshold value (pcf) | |
|---|---|---|
|  | G. trabeum | T. versicolor |
| Creosote | 5–8 | >2 |
| Bio-oil | 20 | 4–13 |

Figure 7:
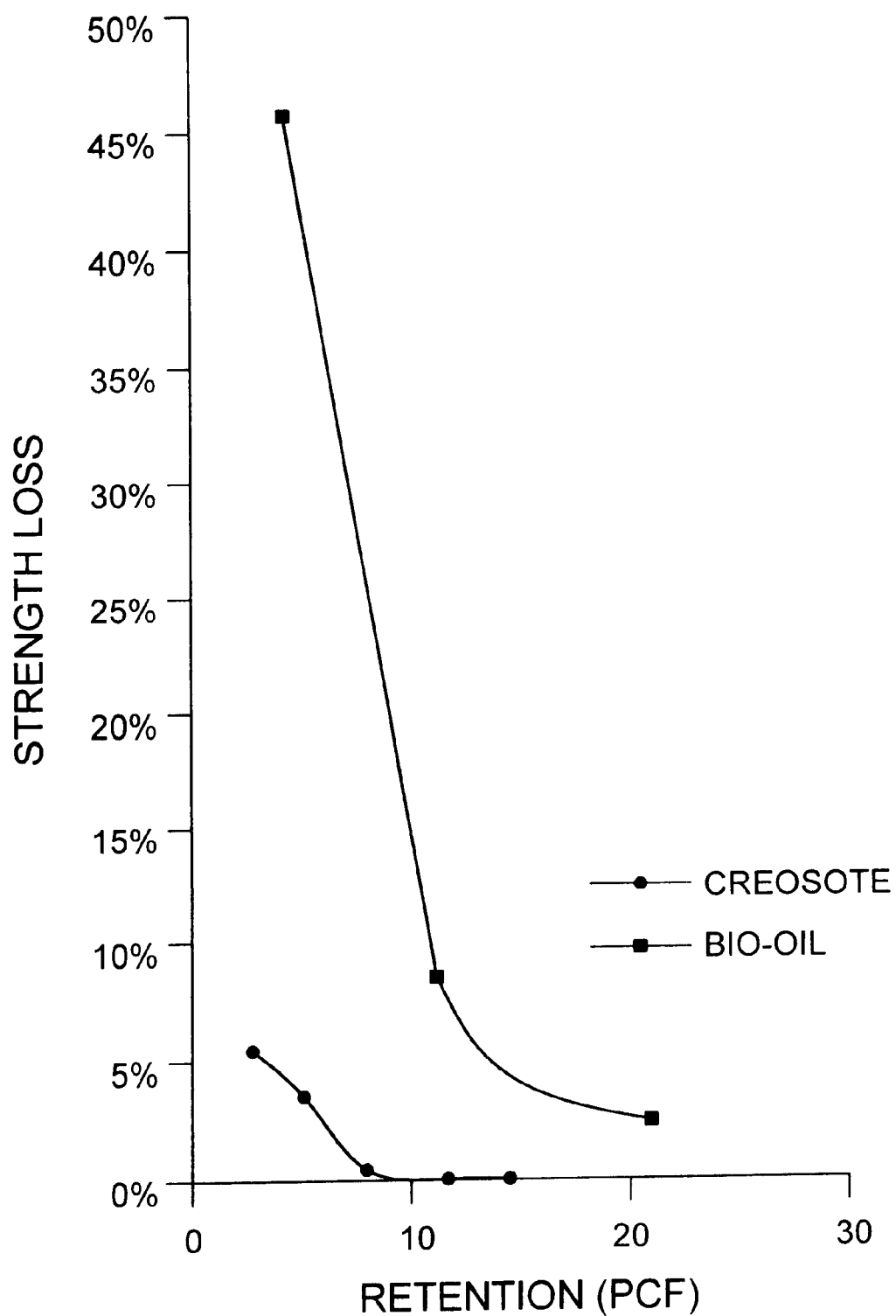
FIG. 7 shows the loss of strength of samples treated with either bio-oil obtained from hardwood, or virgin creosote, analyzed using soil-block tests with brown rot fungus.

FIG. 7 is a plot of strength loss versus preservative retention for creosote (standard) and bio-oil (R151) when exposed to brown-rot fungus. The toxicity threshold for creosote is 9 pounds per cubic foot (PCF) and approximately 15 PCF for bio-oil. The curves represent the mean strength loss over eight (8) samples for each retention. The % compression and stress loss for the brown rot fungus control samples was 37.3 and 63.2 for methylene chloride and methanol treated wafer blocks, respectively. The control values for white-rot fungus were 79.4 and 66.4 for methylene chloride and methanol, respectively.

Creosote at a retention of 2.8 PCF is more potent preservative than bio-oil at 3.5 PCF retention. At 9 PCF creosote completely protects the wood against brown-rot decay. At 20 PCP bio-oil provides some protection against brown-rot.

Figure 8:
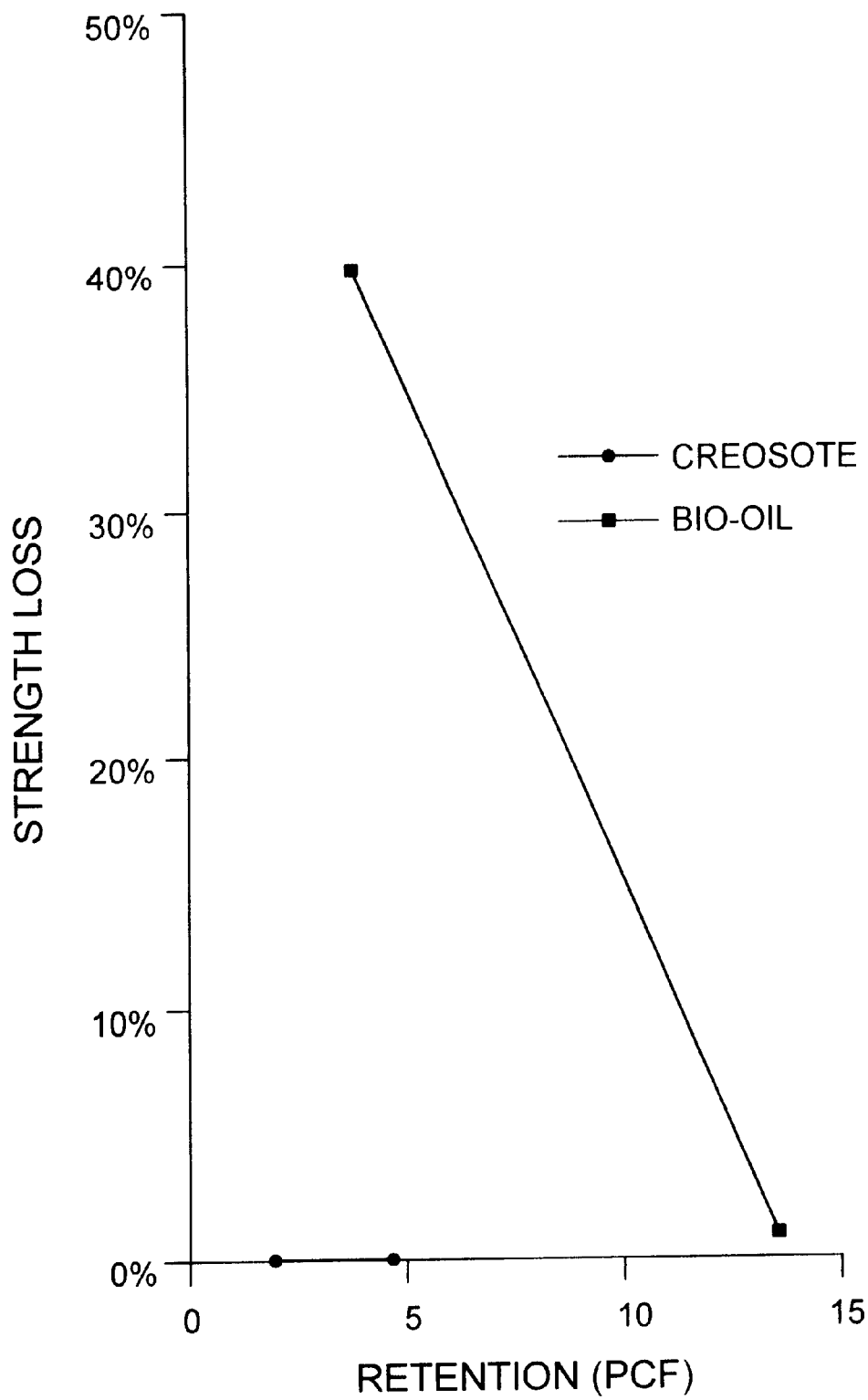
FIG. 8 shows the loss of strength of samples treated with either bio-oil obtained from hardwood, or virgin creosote, analyzed using soil-block tests with white rot fungus.

Bio-oil is more effective against white-rot decay. Bio-oil affords nearly total protection against decay at retentions in excess of 13 PCF (see FIG. 8). Creosote provides the same level of protection at a retention of 2.4 PCF.

Bio-oil exhibits sufficient activity against these two fungi. It is also possible that formulations comprising traditional preservatives, for example, penta or creosote, and bio-oil may enhance the activity of these preservatives. Formulations comprising bio-oil and penta are desired as the bio-oil component complements and improve penta's activity against white-rot fungi.

There is also a physical improvement in wood treated with bio-oil. Without wishing to be bound by theory, the physical improvement in wood treated with bio-oil may arise from bio-oil solidifying on the surface of the wood and this may act as a physical barrier to rot causing fungi. This feature may also be beneficial in formulations comprising traditional preservatives and bio-oil, in that depletion rates of these preservatives, for example, penta-based preservatives, are reduced in the presence of bio-oil.

Example 3
Bio-Oil/Creosote mix Preservative

As indicated in example 1, creosote passes through the pyrolysis process relatively untouched. Therefore, samples of bio-oil obtained as described in Example 1 (R162) were tested using soil block testing (see example 2).

The effectiveness of bio-oil derived from the pyrolysis of railway ties was similar to that of commercial grade creosote. Table 7 lists the toxicity thresholds for brown-rot and white-rot fungi when the wood is treated with big-oil and creosote. The test results show that bio-oil and creosote have essentially the same toxicity threshold when tested with the two fungi. Bio-oil appears to be more effective against white-rot fungus.

TABLE 7

RAILWAY TIE DERIVED BIO-OIL

| Formulation | Fungus | Toxicity Threshold(PCF) |
|---|---|---|
| Creosote | Brown-rot | 1.4 |
| Bio-Oil | Brown-rot | 1.9 |
| Creosote | White-rot | 0.7–0.8 |
| Bio-Oil | White-rot | 0.2–0.3 |

Figure 9:
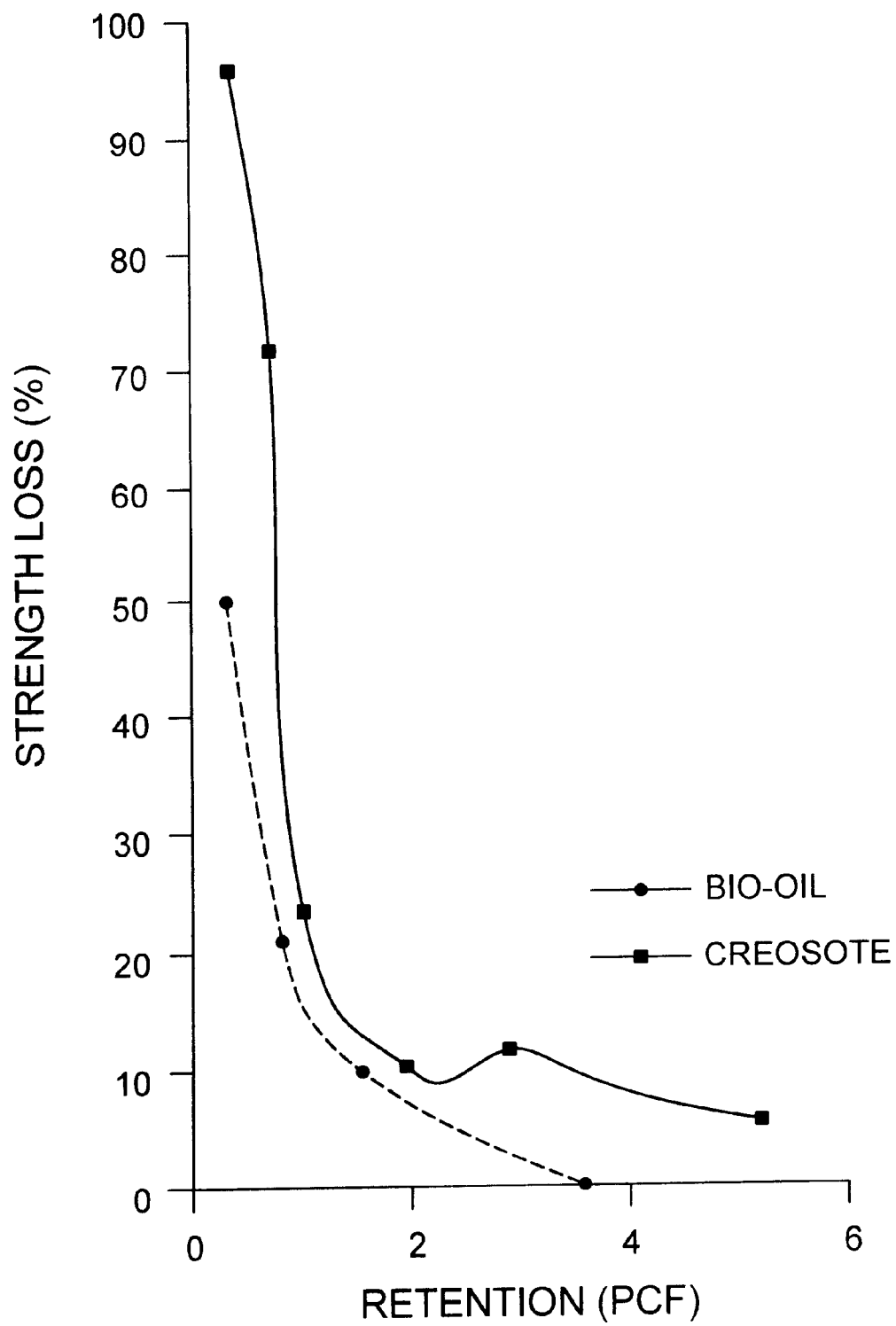
FIG. 9 shows the loss of strength of samples treated with either bio-oil obtained from creosote treated wood (railway-ties), or virgin creosote, analyzed using soil-block tests with brown rot fungus.
Figure 10:
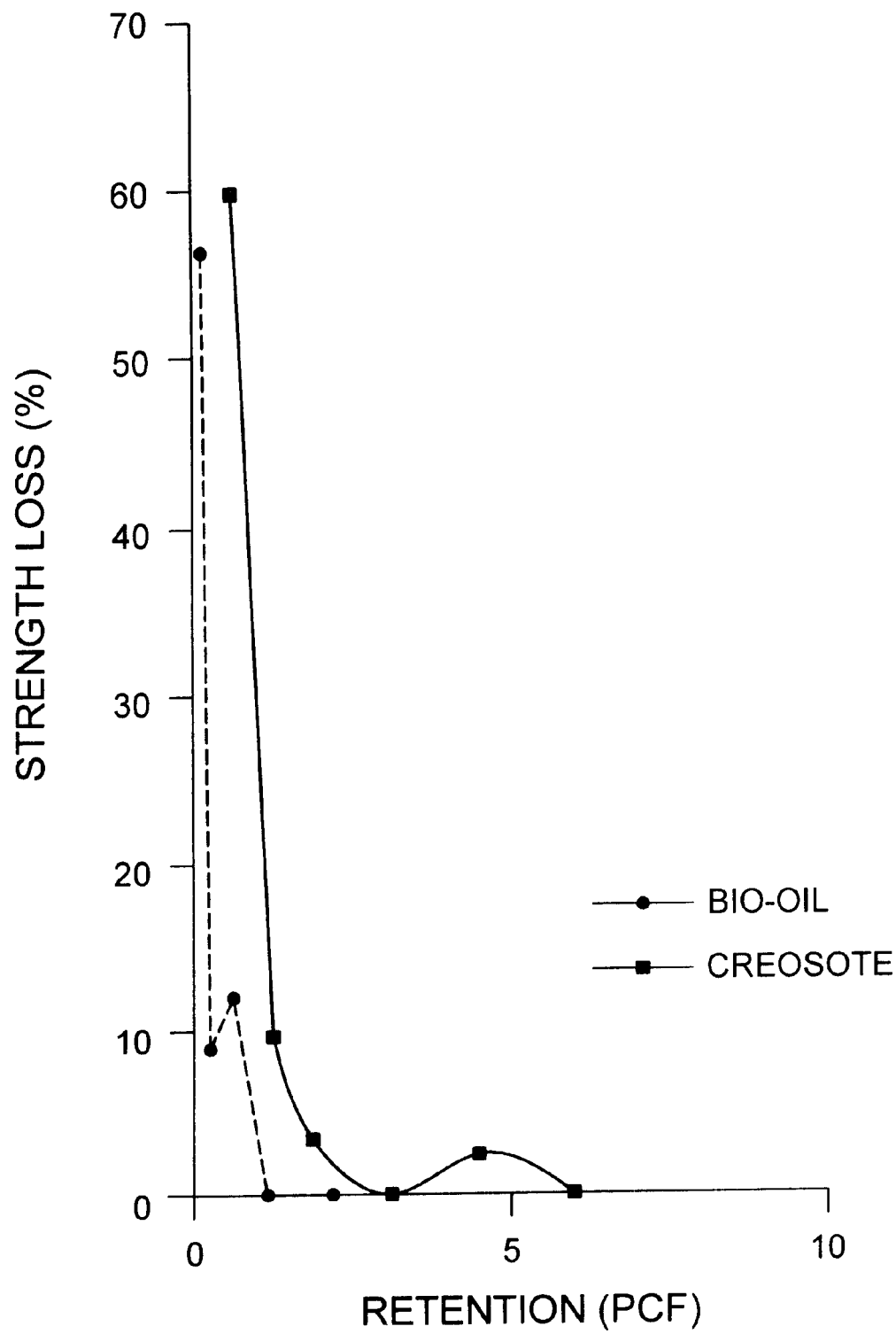
FIG. 10 shows the loss of strength of samples treated with either bio-oil obtained from creosote treated wood (railway-ties) or virgin creosote, analyzed using soil-block tests with white rot fungus.

FIGS. 9 and 10 show the decrease in strength loss for brown and white rot fungi respectively. In both cases the big-oil showed slightly better preservative performance than creosote.

Bio-oil also appears to improve the strength of treated wood, and as a result bio-oil may have an additional advantage over traditional preservatives. Tests with bio-oil concentrations greater than 50% significantly increased the compressive strength of wood. The final compressive strength exceeded the load cell capacity and was not measured. These observations indicate that there is a trend towards increasing the strength of the wood with increasing retention of bio-oil. Furthermore, wafers treated with bio-oil and processed using the soil-block test subject to compression strength analysis (as would be regularly done for soil-block analysis) either directly, or following autoclaving further demonstrates that bio-oil increases the strength of bio-oil treated wood (Table 8). The heat during autoclaving does not have any effect on the strength of the wood samples.

TABLE 8

Average strength increases of wood samples treated with bio-oil.

| Sample | Average Retention (pcf) | Conditioning | Strength Increase (%) |
|---|---|---|---|
| 1–10 | 7.502 | autoclaved | 15.76 |
| 11–20 | 7.358 | ambient | 12.98 |
| 21–30 | 19.581 | autoclaved | 31.4 |
| 31–40 | 22.271 | ambient | 27.07 |
| 41–50 | 35,524 | autoclaved | 34.69 |
| 51–60 | 36.738 | ambient | 34.3 |

This latter finding is of significance as current forest management practices tend to accelerated growth of new trees which results in growth rings that are wider apart. Without wishing to be bound by theory, it is thought that this type of wood has inferior strength properties to wood obtained from old growth forests. An improvement in the strength of wood through the use of a bio-oil preservative would result in a fundamental advantage over traditional preservatives. For example, utility poles derive the majority of their strength from the outer portion of the pole. A small improvement in the outside strength can result in a significant increase in the overall carrying capacity of the pole. Strength improvements could also reduce plate crushing on railway ties and minimize premature failure of railway ties.

Example 4
Bio-Oil as a PCP Carrier

Several traditional preservatives are mixed with other solvents as carriers. For example, penta-based preservatives are combined with a co-solvent such as ketone bottoms. As indicated in Example 2, the fungicidal effect of bio-oil, which is effective against white-rot fungus, may compliment the fungicidal activity of penta which is weak in this regard. Therefore, the addition of bio-oil to penta-based preservatives was examined.

Varying concentration of penta or creosote were added to bio-oil, heated to dissolve, followed by cooling to room temperature. The resultant formulations were tested for efficacy using the soil block test.

Initial results indicate that the toxic threshold for bio-oil/penta formulations are lower than penta or bio-oil alone for both white-rot and brown-rot fungi.

Example 5
Treated Wood

As shown in Example 3, Bio-oil from creosote-treated wood is an effective wood preservative and can be easily applied to wood. Since bio-oil is a low viscosity fluid at ambient temperatures, the uptake of the bio-oil preservative by wood was examined.

Small blocks of wood were subjected to a vacuum and the bio-oil preservative was readily accepted into the wood pores upon release of the vacuum. The impregnation of wood by bio-oil was also examined using the normal pressure processes. Using a full-cell process, several bio-oil temperatures, press times (30 min, 1 hr and 4 hr), and pressures (150 psig and 200 psig) were examined using kiln-dried southern yellow pine sapwood that were end-sealed. Solution retention was determined by weight gain and visual inspection of penetration of cut samples.

Initial results indicate that bio-oil is taken up by wood when maintained in a positive pressure environment over a range of temperature, including ambient temperature. Penetration and retention of die preservative by the wood can be achieved at relatively low pressure and temperature, however, elevated temperature and pressure can also be used as required.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A bio-oil composition comprising derivatized lignin, alcohol, natural organic acids, carbonyls and at least one compound selected from the group consisting of:

1-(or 2-)methylnapthalene
1,1'-biphenyl, or acenaphthalene, or 2-ethenyl-naphthalene,
3-hydroxy-4-methoxy (or 4-hydroxy-3-methoxy)-phenol,
dibenzofuran,
4-hydroxy-3-methoxy-benzeneacetic acid,
9H-fluorene or 1H-phenalene,
phenanthrene or anthracene,
fluoranthene or pyrene, and;

wherein said bio-oil is a wood preservative, and is liquid at room temperature.

2. The bio-oil composition of claim 1 further comprising 2-methoxy-4-methylphenol and 3,4-dimethoxybenzoic acid.

3. The bio-oil composition of claim 2 further comprising at least one of the following compounds:

2-methoxyphenol,
4-ethyl-2-methoxyphenol or 1,4-dimethoxy-2-methylphenol,
2-methoxy-5-(or 4,6) (1-propenyl)phenol,
2,6-(or 3,4-)dimethoxyphenol,
2-methoxy-5-(or 4, or 6) (1-propenyl)phenol,
4-hydroxy-3-methoxybenzoic acid or 2,5-dimethoxybenzyl alcohols
(1,1-dimethylethyl)-1,2-benzenediol or 1-(4-hydroxy-3-methoxyphenyl)ethanone,
2,6-dimethoxy-4-(2-propenyl)-phenol, and
3,440 (or 3,3' or 4,4')-1,1'-biphenyl.

4. A wood product treated with the bio-oil composition of claim 3.

5. A wood product treated with the bio-oil composition of claim 2.

6. The bio-oil of claim 1 further comprising the following compounds:

2-methoxyphenol,
2-methoxy-4-methylphenol,
4-ethyl-2-methoxyphenol or 1,4-dimethoxy-2-methylphenol,
2-methoxy-5-(or 4,6) (1-propenyl) phenol,
2,6-(or 3,4-)dimethoxyphenol,
2-methoxy-5-(or 4, or 6) (1-propenyl) phenol,
4-hydroxy-3-methoxybenzoic acid or 2,5-dimethoxybenzyl alcohols
(1,1-dimethylethyl)-1,2-benzenediol or 1-(4-hydroxy-3-methoxyphenyl)ethanone,
3,4-dimethoxybenzoic acids
2,6-dimethoxy-4-(2-propenyl)-phenol, and
3,4' (or 3,3' or 4,4')-1,1'-biphenyl.

7. A wood preservative composition comprising said bio-oil composition of claim 1 and a water-based wood preservative, or an oil-based wood preservative, or a combination of a water-based and an oil-based wood preservative.

8. The wood preservative of claim 7, wherein said bio-oil composition comprises an oil-based wood preservative.

9. The wood preservative of claim 8 wherein said oil-based wood preservative is selected from the group consisting of creosote or pentachlorophenol.

10. The wood preservative of claim 9 wherein said oil-based wood preservative is creosote.

11. The wood preservative of claim 9 wherein said oil-based wood preservative is pentachlorophenol.

12. A method of preparing the wood preservative composition of claim 7 comprising, processing treated wood using a fast pyrolysis reactor, and obtaining said bio-oil composition.

13. The method of claim 12 wherein said treated wood comprises creosote.

14. A wood product treated with said bio-oil composition obtained using the method of claim 13.

15. The method of claim 12 wherein said treated wood comprises pentachlorophenol.

16. A wood product treated with said bio-oil composition obtained using the method of claim 15.

17. A wood product treated with said bio-oil composition obtained using the method of claim 12.

18. A method of preparing the wood preservative composition of claim 7 comprising, heating said bio-oil and adding said water-based wood preservative, or oil-based wood preservative, or a combination of a water-based and an oil-based wood preservative to said bio-oil, and cooling said wood preservative composition to room temperature.

19. A method of sealing a wood product comprising treating said wood product with said wood preservative composition of claim 7.

20. A method of increasing the strength of a wood product comprising treating said wood product with said wood preservative composition of claim 7.

21. A wood product treated with the bio-oil composition of claim 1.

22. A method of sealing a wood product comprising treating said wood product with said bio-oil composition of claim 1.

23. A method increasing the strength of a wood product comprising treating said wood product with said bio-oil composition of claim 1.

24. A method of preserving wood comprising, applying a bio-oil to said wood, said bio-oil comprising derivatized lignin, alcohol, natural organic acids, and carbonyls, wherein said bio-oil is liquid at room temperature, and is not an adhesive resin.

25. The method of claim 24, wherein said bio-oil further comprises 2-methoxy-4-methylphenol and 3,4-dimethoxybenzoic acid.

26. The method of claim 25, wherein said bio-oil further comprises at least one of the following compounds:

2-methoxyphenol,
4-ethyl-2-methoxyphenol or 1,4-dimethoxy-2-methylphenol,
2-methoxy-5-(or 4,6) (1-propenyl)phenol,
2,6-(or 3,4-) dimethoxyphenol,
2-methoxy-5-(or 4, or 6) (1-propenyl)phenol,
4-hydroxy-3-methoxybenzoic acid or 2,5-dimethoxybenzyl alcohol,
(1,1-dimethylethyl)-1,2-benzenediol or 1-(4-hydroxy-3-methoxyphenyl)ethanone,
2,6-dimethoxy-4-(2-propenyl)-phenol, and
3,4' (or 3,3' or 4,4')-1,1'-biphenyl.

27. A wood product treated by the method of claim 26.

28. A wood product treated by the method of claim 25.

29. The method of claim 24, wherein said bio-oil further comprises the following compounds:

2-methoxyphenol,
2-methoxy-4-methylphenol,
4-ethyl-2-methoxyphenol or 1,4-dimethoxy-2-methylphenol,
2-methoxy-5-(or 4,6) (1-propenyl)phenol,
2,6-(or 3,4-) dimethoxyphenol,
2-methoxy-5-(or 4, or 6) (1-propenyl)phenol,
4-hydroxy-3-methoxybenzoic acid or 2,5-dimethoxybenzyl alcohol,
(1,1-dimethylethyl)-1,2-benzenediol or 1-(4-hydroxy-3-methoxyphenyl)ethanone,
3,4-dimethoxybenzoic acid,
2,6-dimethoxy-4-(2-propenyl)-phenol, and
3,4' (or 3,3' or 4,4')-1,1'-biphenyl.

30. A wood product treated by the method of claim 24.

31. A method of increasing the strength of a wood product comprising, applying a bio-oil to said wood, said bio-oil comprising derivatized lignin, alcohol, natural organic acids, and carbonyls, wherein said bio-oil is liquid at room temperature, and is not an adhesive resin.

32. The method of claim 31, wherein said bio-oil further comprises 2-methoxy-4-methylphenol and 3,4-dimethoxybenzoic acid.

* * * * *